(12) United States Patent
Garcia (10) Patent No.: US 11,376,151 B2
(45) Date of Patent: Jul. 5, 2022

(54) GRAVITY INDEPENDENT MEDICAL DRAINAGE SYSTEMS

(71) Applicant: Maurice Marcel Garcia, San Francisco, CA (US)

(72) Inventor: Maurice Marcel Garcia, San Francisco, CA (US)

(*) Notice: Subject to any disclaimer, the term of this patent is extended or adjusted under 35 U.S.C. 154(b) by 238 days.

(21) Appl. No.: 14/940,589

(22) Filed: Nov. 13, 2015

(65) Prior Publication Data

US 2016/0135982 A1 May 19, 2016

Related U.S. Application Data

(60) Provisional application No. 62/079,462, filed on Nov. 13, 2014.

(51) Int. Cl.
*A61M 27/00* (2006.01)
*A61F 5/44* (2006.01)
*A61M 1/00* (2006.01)

(52) U.S. Cl.
CPC ......... *A61F 5/4404* (2013.01); *A61M 1/0023* (2013.01); *A61M 1/80* (2021.05); *A61M 27/00* (2013.01); *A61M 2205/3334* (2013.01); *A61M 2206/16* (2013.01); *A61M 2210/101* (2013.01)

(58) Field of Classification Search
CPC .............. A61M 1/0023; A61M 1/0066; A61M 2205/3334; A61M 2206/16; A61M 2210/01; A61M 27/00
See application file for complete search history.

(56) References Cited

U.S. PATENT DOCUMENTS

| 3,705,644 A | * | 12/1972 | Kawchitch | B65G 33/26 |
| | | | | 198/664 |
| 4,957,504 A | * | 9/1990 | Chardack | A61M 1/1031 |
| | | | | 415/912 |
| 5,762,599 A | | 6/1998 | Sohn | |
| 5,971,996 A | * | 10/1999 | Tugendreich | A61B 17/42 |
| | | | | 128/898 |
| 8,215,477 B2 | * | 7/2012 | Basaglia | B30B 11/246 |
| | | | | 198/666 |
| 2005/0027265 A1 | * | 2/2005 | Maki | A61B 17/32037 |
| | | | | 604/267 |

(Continued)

OTHER PUBLICATIONS

Unknown Author, "FDA Clears AtheroMed's Phoenix Atherectomy System to Treat Peripheral Artery Disease," Enodvascular Today, Jan. 27, 2014, Evtoday.com.

*Primary Examiner* — Kai H Weng (57) ABSTRACT

Provided herein are medical drainage systems comprising structures to prevent blockages within drainage tubing, especially medical drainage tubing, for example caused by debris or airlocks. The novel systems of the invention employ, in some embodiments, elements of the Archimedian screw. The Archimedian screw elements comprise a rotating conveyer present in the tubing which promotes continuous flow of material through the tubing and prevents the formation of dependent loops and other blockages. The systems of the invention may be employed in diverse contexts, including urinary catheter drainage systems and thoracostamy systems. The systems of the invention, being gravity independent, may also be employed for the drainage or a movement of materials in space and other low gravity environments.

16 Claims, 5 Drawing Sheets

(56) References Cited

U.S. PATENT DOCUMENTS

2007/0100196 A1* 5/2007 LaRose ................ A61M 1/101
　　　　　　　　　　　　　　　　　　　　　　600/16
2012/0323144 A1* 12/2012 Coston ................ A61M 1/0066
　　　　　　　　　　　　　　　　　　　　　　600/581

* cited by examiner

GRAVITY INDEPENDENT MEDICAL DRAINAGE SYSTEMS

CROSS-REFERENCE TO RELATED APPLICATIONS

This application claims the benefit of priority to U.S. Provisional Application Ser. No. 62/079,462 entitled "Gravity Independent Medical Drainage Systems," filed Nov. 13, 2014, the contents which are hereby incorporated by reference.

STATEMENT REGARDING FEDERALLY SPONSORED RESEARCH OR DEVELOPMENT

Not applicable

BACKGROUND OF THE INVENTION

Drainage of bodily fluids is necessary in various contexts. For example, urinary catheters are intended to provide continuous drainage of the bladder and chest tubes are intended to provide continuous drainage of and suction to the thoracic cavity, respectively. Systems such as the Foley urinary catheter and standard chest tube systems are widely used to implement such drainage. However, these systems are prone to problems that impede efficient and continuous drainage, with negative consequences for patients. Furthermore, such systems can become physically obstructed (clogged) with tissue (e.g. blood clots) and/or debris (e.g. stones, pus).

A major issue in drainage systems is the presence of a dependent loop or air-lock. This occurs when air bubbles in the tubing form in advance of draining fluid, for example when the tubing is coiled or bent such that drainage must occur against gravity. The presence of a dependent loop in the tubing will substantially increase resistance to flow, requiring additional driving pressure to overcome that resistance and allow air and fluid to flow through the tubing and completely out of the drainage system. Pressure in excess of the vertical height of the fluid within the dependent loop is required to restore flow, leading to backup of fluid and potentially dangerous back-pressures.

For example, in urinary drainage systems, standard catheter and drainage tube systems are prone to frequent air-locks and discontinuous flows, for example, as quantified in Garcia et al., 2007, Traditional Foley Drainage Systems: Do They Drain the Bladder?, J Urology, 177:203-207. The failure of conventional urinary drainage systems to provide effective and continuous drainage presents various problems. One problem is that blockages and back pressures can result in the back-up of urine into the bladder, which increases patient discomfort, potentially causes injury, and presents a serious risk of infection.

Another major problem with discontinuous flow in urinary drainage systems is that this compromises the ability to accurately monitor patient urine output and composition. In some contexts, it would be advantageous to monitor a patient's real-time urinary output, however, discontinuities in flow negate accurate volumetric measurements, as pooled urine within drainage tubes will flow intermittently and not in real time. Additionally, in some contexts it is desired to measure metabolites and other biomarkers in urine in real time as assessments of patient health, by sampling urine from bladder drainage systems at regular intervals or continuously. When air-locks and other factors create discontinuous flows, real time monitoring of biomarkers is compromised, because urine is not flowing to sampling devices as produced, but is pooling and flowing intermittently and/or is admixed with older urine which has pooled. Accordingly, there is a need in the art for systems that effectively empty the bladder and which create an uninterrupted conduit to sampling vessels or detectors.

Pumps have been utilized to apply suction, which aids in the clearing of air-locks. However this solution is less than optimal due to the bulk and expense of complicated pumping devices.

Accordingly, there is a need in the art for medical drainage systems which efficiently prevent air-locks or which can overcome the resistance created within dependent loops in drainage tubing. The inventions described herein provide the art with such solutions, which are inexpensive, low profile, and effective.

Effective drainage also becomes an issue in other contexts as well, for example in space travel. In the absence of normal gravitational forces, fluid and/or semi-solid material to be drained forth from the body is currently often moved by air-suction, but this requires subsequent filtering of air used for this purpose, which is complicated and costly. Accordingly, there is a need in the art for gravity independent drainage systems that can be employed in low gravity environments.

SUMMARY OF THE INVENTION

Disclosed herein are novel devices that employ an Archemedian screw element to mechanically prevent obstructions and airlocks in drainage tubing. The devices described herein allow for drainage of fluid to be achieved independent of gravity. The devices of the invention may be utilized in catheter systems for the drainage of urine, in chest tube systems, and in other contexts. The inventions herein are also directed to the need for unobstructed continuous drainage of materials in a weightless environment, such as at extremely high altitudes and/or in space. Instead, human wastes and other fluids and solids requiring transport in space can be moved by mechanical force using the devices and methods described herein.

BRIEF DESCRIPTION OF THE DRAWINGS

FIG. 1 depicts a prior art Archimedean screw. In the solid plane configuration, the screw portion rotates within the hollow tube. In the fixed configuration, the plane of the screw is attached to the inner walls of the tube and the whole assembly rotates.

FIG. 6.

DETAILED DESCRIPTION OF THE INVENTION

Part I

Overview of the Inventive Concept

The invention encompasses the use of what is known as the "Archimedean screw" to aid in medical drainage. The Archimedean screw is a device reportedly designed and made by the Greek mathematician Archimedes in 3 BC. Based on archeological evidence, however, some historians believe it was actually first invented much earlier, in Assyria.

Figure 1:
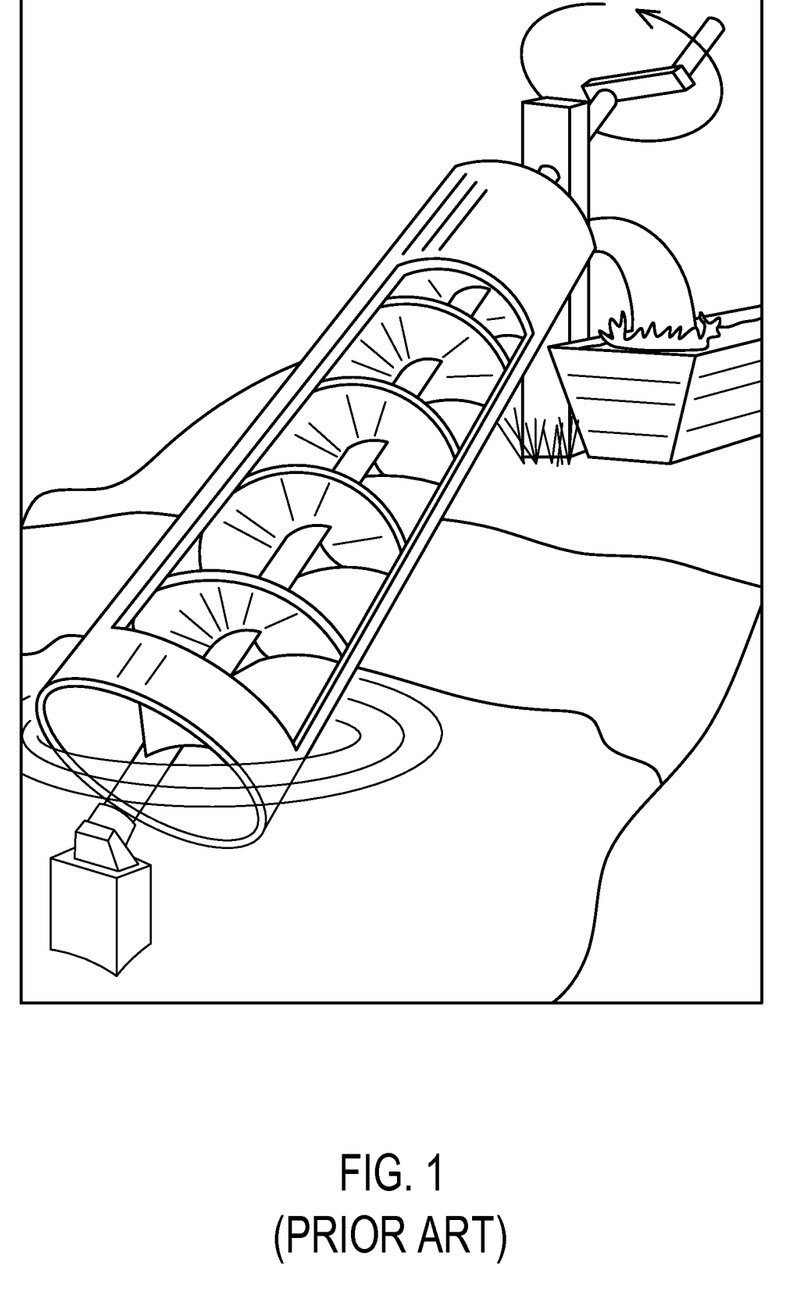

In one implementation, an Archimedean screw consists of a solid plane screw, as depicted in FIG. 1. The screw comprises an auger, or an angled, continuous helical surface surrounding (and typically attached to) a central shaft inside a hollow pipe. Shaftless screws are also known. Rotation of the screw conveys liquids, slurries, and solids along the axis of the shaft by a continuous lifting or scooping force created by the angle of the rotating auger. Auger angles may range from 1-90 degrees (measured as the angle of rise between the edge of the screw plane from the central shaft), with typical auger angles in the range of 15-60 degrees. In some embodiments, the plane of the screw is angled in the direction of transport, i.e. "forward-facing."

In one implementation of the Archimedean screw, herein referred to as the "solid plane configuration," the screw rotates freely within the pipe. The contact surface between the screw and the pipe in general does not need to be perfectly watertight, so long as the amount of liquid being conveyed at each turn is larger than the amount of liquid leaking out of each section of the screw per turn (determined by the angle of the auger, diameter of the auger, and the rate of rotation). Liquid from one section leaks down into the next lower section along the entire length of the screw, such that an equilibrium is established.

In an alternative implementation of the Archimedean screw, herein referred to as the "fixed configuration," the outer edge of the screw is attached to the wall of the pipe and the inner edge of the plane of the screw is attached to the shaft, and the entire tube rotates to provide the conveying action. An Archimedean screw of the fixed configuration appears identical to the Archimedean screw depicted in FIG. 1, except that it is understood that the plane of the screw is attached to the inner wall of the pipe and the entire apparatus rotates.

Figure 2:
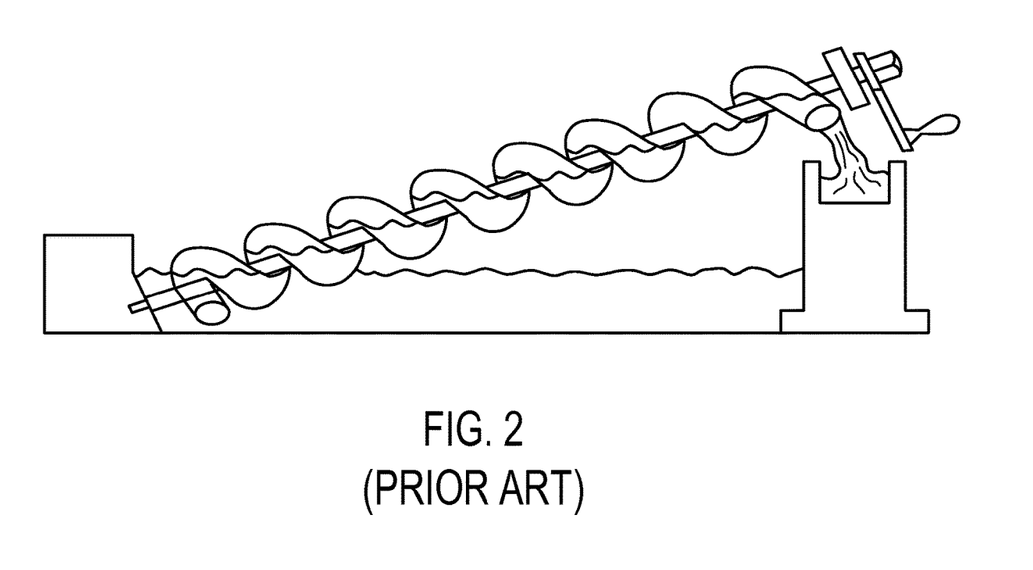
FIG. 2 depicts a prior art tubular Archimedean screw.

In a third implementation of the Archimedean screw, herein referred to as the "tubular configuration," the screw comprises a helical tube which rotates, optionally affixed to a central shaft. As the tube is rotated about its long axis, fluid that enters the proximal mouth of the hollow tube will be carried to the distal end of the tube, against gravity. An exemplary Archimedean screw of the tubular configuration is depicted in FIG. 2.

Modern implementations of the Archimedean screw are utilized in various contexts, for example industrial contexts. Typically referred to as "screw feeds," "screw conveyers," or "auger conveyers," these devices are used to lift dry particulate materials (e.g. grain) or slurries (e.g. sewage). In some devices, the screw assembly is flexible, allowing the pipe and screw to bend to some degree while maintaining effective conveyance of material against gravity. Various implementations of flexible Archimedean screw conveyers are known in the art, for example as described in U.S. Pat. No. 2,830,695, "Flexible screw conveyor," by Fennimore; US Patent Publication Number 20020088691, "Flexible screw conveyor with center tensioning core," by Hesketh; U.S. Pat. No. 3,709,357, "Flexible helical conveyor for liquids," by Brown, and European Patent Application Publication Number EP0450101, "Flexible screw and transfer apparatus using the same," by Ohtsiji.

In the present invention, a flexible Archimedean screw is adapted for use in drainage tubes wherein an Archimedean screw element comprising a flexible material or a jointed structure is encased in a housing of flexible tubing. As used herein, an "Archimedean screw element" may comprise an Archimedean screw of any configuration, including the solid plane configuration, the fixed configuration, the tubular configuration, or a hybrid configuration incorporating elements of two or more of the foregoing.

In some embodiments, a single Archimedean screw element is present in the tubing. In alternative embodiments, multiple Archimedean screw elements are present in series, optionally separated by sections of standard tubing, each such element having an independent driving mechanism.

Various geometries of Archimedean screws and/or screw conveyers are known in the art, and any such implementation of the screw concept in medical drainage tubing or low-gravity transport contexts is within the scope of the invention. For example, various screw designs and modifications which enhance the screw element's transport of liquid materials are described in Rorres, 2000, "The turn of the screw: Optimal designs of an Archimedes screw," Journal of Hydraulic Engineering, 126:72-80. For example, in some implementations, radial ridges or walls may be present on the forward-facing surface of the screw plane (i.e. facing in the direction if liquid transport), such structures extending substantially radially from the shaft to the outer edge of the screw plane. The use of such ridges or walls aids in the prevention of backwards flow of liquids when transporting against gravity, as fluid is trapped in the pocket defined by the junction of the wall and the flat blade surface. In another embodiment, catchment structures are present on the forward-facing surface of the screw plane, such as grooves, cups, wells or any other structure capable of catching liquid and aiding its transport against gravity.

For clarity, the terms "distal" and "proximal," as used herein, will refer to the location of a feature or element of a conveyor system with respect to the source of material being transported by the system. In the medical context, the proximal end is the source of material, being the patient. For example, in the case of a urinary drainage tube connecting an indwelling catheter to a urine collection vessel, the connection to the catheter output port will be the proximal end of the tubing while the connection to the urine collection vessel will be the distal end of the drainage tube.

The drainage tubing of the invention is connected on its proximal end with the source of liquid or other material to be drained (i.e. at the patient) and on its distal end with the collection vessel. The Archimedean screw element is rotated by a mechanical turning apparatus which may be connected to either the proximal or distal end of the housing, the end of the screw opposite the drive apparatus may be anchored, for example by a plate with a hole in which the shaft rotates (the plate being perforated so liquids can pass through), or it may rotate freely within the tubing without anchorage.

The housing may comprise any flexible tubing material known in the art, for example medical tubing such as latex or silicone, polytetrafluoroethylene, fluorinated ethylene propylene, perfluoroalkoxy alkanes ethylene tetrafluoroethylene, and other materials known in the art for use in medical grade tubing. Tubing inner diameters may vary, for example between 5 and 10 mm. For example, a typical urinary drainage bag has an inner-diameter of between 5-10 mm (averaging~8 mm) with an outer diameter of about 11 mm. A typical chest-tube drainage system has an inner diameter of about 9-10 mm, and an outer diameter of about 12 mm. The screw element should have a diameter which is only slightly less than the inner diameter of the tubing, for example 0.1 to 1 mm. Screws with a diameter close to the inner diameter of the tubing will experience more friction but less leakage, while screws with a significant space between the edge of the screw and the inner wall of the tubing will experience greater leakage but less friction.

The screw portion of the conveyer may comprise any flexible or malleable polymeric material. For example, materials such as polypropylene, polyethylene, silicon rubber, polyurethane, epoxy resin, polymethylmethacrylate, polyamides, polyimides, elastomers, fluorocarbons, nylons, polyvinyl and poly olefin compounds may be used. For example, closed cell resin foams, such as polyurethane foams may be utilized. The materials will preferably be water resistant and low friction to prevent water logging and contamination and to promote easy turning of the screw within the tubing. Non-tacky silicone materials may also be used. Low-friction coatings may be applied to the screw, the inner wall of the housing, or both, to ease turning of the screw element within the housing. Exemplary coatings for decreasing friction between the edges of the screw and the inner diameter of the tubing include TEFLON™, PTFE, and other coatings known in the art.

Preferred materials are for the Archimedean screw element are sanitary, non-leaching (so as to not contaminate samples drawn from the drainage), and low-friction (to ease the turning of the screw within the housing). The material will, in some embodiments, be intended for single use and disposal after use. In other embodiments, the screw and tubing will be intended for multiple uses and will be composed of materials that can be sterilized, e.g. by autoclaving or chemical sterilization. The Archimedean screw element and/or the housing may further comprise antimicrobial coatings, for example BARDEX™ or BACTI-GUARD™ silver-based coatings (Bard Medical).

In some embodiments, the screw is made of a single material. In other embodiments, the plane of the screw is made of one material and is affixed around a central shaft made of another material, for example a semi-rigid metal wire or plastic spine which enables efficient rotation of the screw from the drive motor. For example, titanium or nickel titanium alloys (e.g. nitinol) may be used.

In some embodiments, the Archimedean screw element comprises a single piece of material. In alternative embodiments, the Archimedean screw element comprises a modular design, with multiple segments connected in series. Such individual segments may be made of rigid materials, so long as the resulting chain they form is flexible. A chain of such elements will be referred to as having a rear-to-forward orientation, in the direction of transport. Each such segment will comprise a section of helical screw plane and forward- and rear-facing connector structures or means which connect the segment to additional segments at its two ends. Such connectors will comprise a structure or means of receiving rotational forces from the previous segment in the chain (i.e. that which is disposed towards the motorized drive means) and transferring such rotational forces to the next segment (i.e. the segment distal to the motorized drive means), such that a segment is turned by the previous segment and also turns subsequent segments in the chain. In some embodiments, connectors will comprise joints or other structures which enable some degree of translational movement between segments, for example in the form of pin joints, ball-and-socket joints, hinge joints, or any other structure capable of connecting two segments such that they will move independently to some degree. The use of such joints will impart flexibility to the chain of linked segments.

The screw may be made by any means, for example by injection molding, blow molding, printing, or machining, or by any other fabrication means known in the art.

The mechanical drive means may be any motorized means to turn the screw portion. For example, direct mechanical rotation of the screw by the motor may be achieved. In another embodiment, the screw comprises one or more magnetic or ferrous elements and is turned by the action of a rotating magnet or magnetic force external to the housing. Preferred drive means comprise small electric motors, for example battery powered motors, which may comprise small, lightweight, low profile and inexpensive means for turning the screw portion of the apparatus. For example, in one embodiment, the screw is turned by a driver which circumscribes a terminal or intermediate section of the screw and applies a rotational force to the screw, for example by applying direct rotational forces on the shaft. For example, a portion of the shaft may comprise teeth, and the driving means may comprise a cogwheel circumscribing toothed section of the shaft. Any such cogwheel or other lateral drive mechanism which radially occupies the lumen of the tubing will necessarily have vents, pores, openings or other means for fluid to transverse the drive element. The use of a drive means which circumscribes the shaft of the screw element advantageously allows for in-line placement of the driver housing and the ability of fluid to pass through the housing comprising the drive element. In an alternative embodiment, the screw portion of the Archimedean screw element terminates and the shaft extends out of the main drainage lumen, exiting the drainage lumen from a hole or branched connection and entering the drive means.

The mechanical drive means may be connected at either the distal or proximal end of the drainage tube, or at an intermediate section of the tubing. In an alternative embodiment, two drive elements are utilized, one connected to each end of the screw, for example to effect greater torque, for instance when using long sections of tubing or when the friction of rotation is large. In other embodiments, two or more drive units can turn the screw from various positions along of the drainage tube.

The mechanical drive means may be turned continuously, or at regular intervals, depending on the intended use of the drainage system. Rotation rates may be readily calculated based on the volume and flow rate of the drainage material and the capacity of the conveyer. Exemplary rotation rates are in the range of 10-100 RPM.

In one aspect, the screw can be described as having a fixed "moving capacity," representing the length of tubing traversed between screw turns (i.e. the unit length traversed by one revolution of the screw). In another aspect, the screw may be described as having a "moving efficiency," representing the efficiency with which material is moved along the length of the screw. Some degree of leakage between the edge of the screw plane and the inner wall of the tubing will be expected, depending on the nature of the material being moved (e.g. liquid, solid, semi-solid or mixed compositions). For example, a ball bearing will be expected to have a moving efficiency of 100%, whereas a liquid such as water, when moving against gravity, will to some degree drip backwards with each turn, resulting in a moving efficiency of less than 100%. Moving efficiency can be increased by increasing the rate of rotation of the screw such that forward momentum partially or wholly overcomes the effects of backwards leakage. Moving efficiency may also be affected by the angle of the screw, where steeper angles can "cup" or catch a substantial portion of liquid to prevent its backflow, or the presence of catchment structures, as described above.

In space application, as discussed below, gravity drops out as a factor and moving efficiency depends wholly on factors such as viscosity, and the degree to which the matter sticks to the walls or screw blades.

The medical drainage systems of the invention may be utilized in conjunction with sources of suction, for example as described below in thoracostomy drainage systems. In other embodiments, suction is not desirable, for example in the drainage of urine from the bladder. In such cases, the medical drainage systems of the invention may be modified to prevent suction forces from arising by the motion of the screw. For example, in continuous plane screws, the pumping action of the screw may create a vacuum force, especially where the edge of the screw plane is in very tight contact with the wall of the housing. Accordingly, the devices of the invention may comprise drainage tubing having vents (or tubing in connection with a vented structure), as known in the art, e.g. as used in vented Foley catheters. Such vents may comprise pressure release valves, semi-permeable membranes, and other venting systems known in the art to allow air ingress and avoid suction buildup. In a related embodiment, in planar screw embodiments of the invention, the screw surfaces may comprise slits, holes, openings, or pressure sensitive vents in order to allows air ingress into the drainage tubing, in order to maintain the tubing at to ambient air pressure.

In some embodiments, the medical drainage systems of the invention are advantageously combined with other features, systems, and technologies for enhanced drainage performance. For example, the drainage systems of the invention can be combined with technologies described in United States Patent Application Publication Number 20120130949, by Garcia, entitled "Catheter Drainage System. For example the drainage tube can drain into a flat collection bag on or near the floor. In this way, the drain tube tends to avoid loop configurations that result in trapping of air and fluid pockets. In addition, this innovation avoids the relatively high pressures encountered upstream of fluids collected in typical vertically hanging bags. In some embodiments, a fluid trapping loop is prevented in the drainage tube by placing the collection vessel near floor level, with the drainage tube held near floor level by provision of spacers mounted around the drainage tube so that the tube is held off the floor, and preferably held at a level above the inlet port of the collection vessel.

In some embodiments, the screw is replaced with a rotating coil, for example a wire coil resembling a spring. The rotating wire coil may be attached at various attachment points to a central shaft that is rotated, or it may be rotated by motors at it ends with no central shaft. The wire coil typically will have no planar surfaces, in contrast to an auger. Typically, the wire coil does not convey substantial amounts of material. Instead, the function of the rotating coil is to prevent and/or break up solid and semi-solid deposits and blockages in the lumen of the tubing. Additionally, the rotating wire coil may break up airlocks, air bubbles, and other impediments to flow. In some embodiments, the surface of the coil is irregular, textured, or comprises barbs or grooves in order to increase material or fluid adherence. Alternately, the coil may be coated with a hydrophilic material to increase fluid or material adherence.

Part II

Specific Applications

Urinary Catheter Drainage Systems. In one aspect, the invention is directed to the use of Archimedean screw elements to aid in the (1) drainage and/or (2) sampling of urine from an indwelling urinary catheter. Various indwelling urinary catheters are known in the art, for example the Foley catheter. These devices can form efficient conduits for urine entering the bladder to leave the body, via the distal end of the catheter. Catheter drainage ports are typically connected to a long section of drainage tubing which empties into a urine collection vessel, for example a urine collection bag.

In the standard prior art drainage systems, along the path from bladder to collection vessel, urine tends to pool in two places. First, urine may pool at the connection between the catheter and the drainage tubing, due to the constricted opening, air-locks, etc. Also, urine pools within the long drainage tube leading from the catheter output port to the collection vessel due to dependent loops caused by bends or loops in the tubing.

Pooling of urine between the catheter output port and the collection vessel is problematic in that it creates risks of backflow, infection, and bladder injury. In one aspect, the invention is directed to the efficient transport of urine from the bladder to the collection vessel by providing a reliable conduit substantially free of resistance or obstructions. This enables accurate real-time monitoring of urine output and/or biomarkers by removing obstacles to continuous flow, such obstacles being a fundamental limiting factor to real-time monitoring systems.

Figure 3:
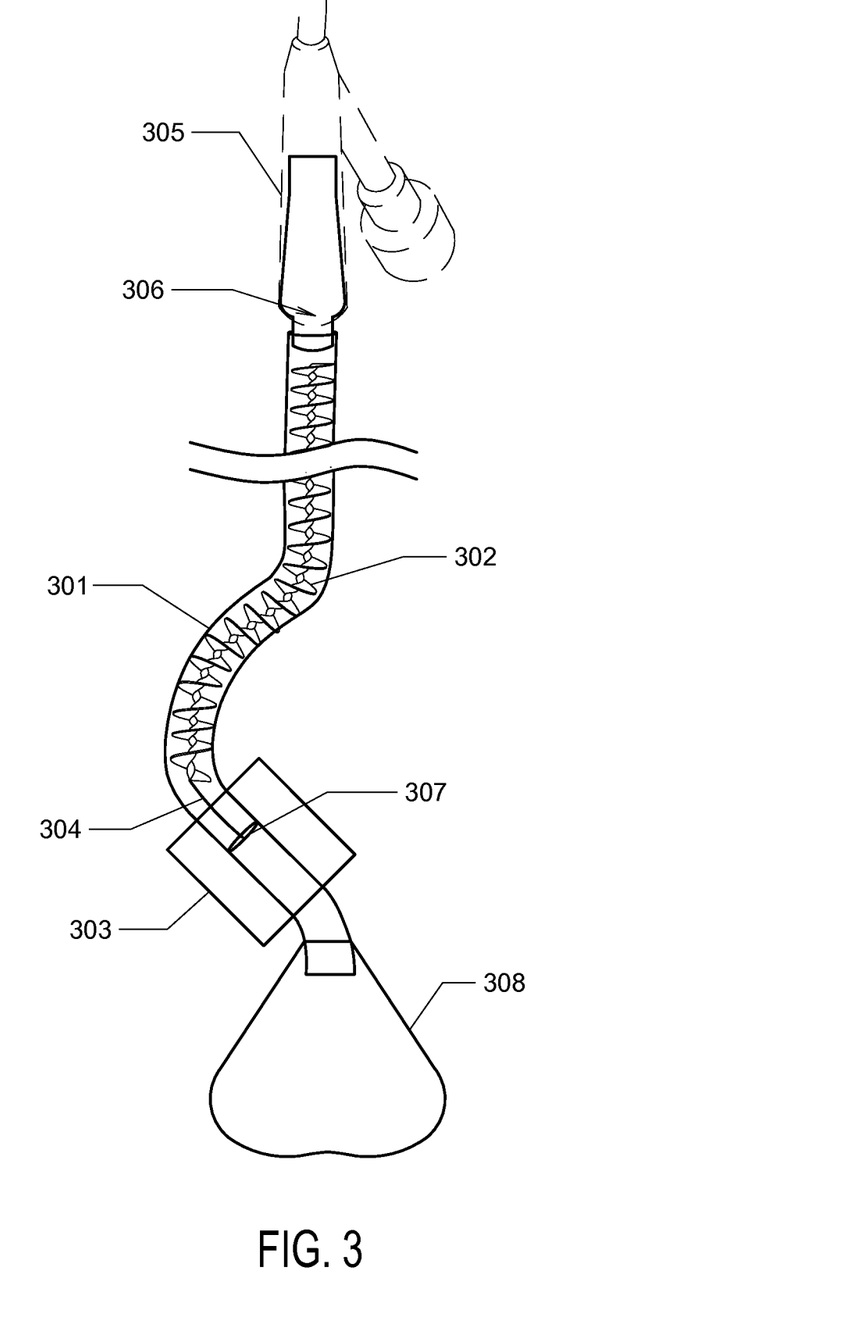
FIG. 3 depicts a schematic diagram of a solid plane Archimedean screw which aids in the drainage of urine or other body fluids. Components depicted in this and the following drawings are not intended to be to scale.

In one embodiment, the invention comprises a drainage tube connecting the catheter output port to the collection vessel in which the entirety or a substantial portion of the drainage tube is cleared by the action of an Archimedean screw. For example, as depicted in FIG. 3, the Archimedean screw element spans substantially the entire length of the drainage tube, providing an efficient conduit for urine from the catheter output to the collection vessel. In alternative embodiments, the Archimedean screw element occupies only a portion of the drainage tube, for example the distal two thirds of the drainage tube's length, where bends in tubing are often experienced. In another embodiment, two or more separate Archimedean screw elements are situated along the span of the drainage tube and work in tandem to create efficient flow. In some implementations, the rotation of the Archimedean screw is continuous. In other embodiments, the rotation of the screw is intermittent and acts to periodically clear potential blockages from air-locks.

An exemplary urinary drainage system is depicted in FIG. 3. The drainage system comprises a drainage tube (301) within which an Archimedean screw element (302) is present. The screw is driven by a motor, residing in a housing (303), which is connected to and rotates the central shaft of the screw (304) by the action of a drive element (307). Where the drive element is located within the lumen, the drive element may be perforated or otherwise shaped or configured such that urine may pass through or around it. The proximal end of a urinary catheter (305) is connected to the drainage tube by a connector (306), which may comprise any fitting or union known in the art for connecting catheter output ports to drainage tubing. At the distal end of the screw, the urine passes through the motor housing (303) and enters into a urine collection vessel (308).

In a second aspect, the devices and the methods of the invention are directed to real-time urine collection and analysis. A number of systems are known in the art which collect urine from the patient for the performance of various analyses, such as measurement of urine volume. For example, the Criticore™ system (Bard Medical) and the URINFO™ system (FlowSense) may be utilized for continuous measurement of patient urinary output volume. The ability of such systems to provide real-time monitoring of patient health is compromised when urine output is not measured in real time due to air-locks in the system which create discontinuities in flow, such that older urine pools and mixes with fresher urine.

Accordingly, the devices and methods of the invention may be applied in continuous urinary output volume monitoring by providing a conduit free of obstructions, wherein fresh urine is continuously removed from the catheter drainage port and efficiently routed to a sampling device. Such systems may be configured as described above for efficient drainage, for example with Archimedean screw elements which span a portion of the drainage tube, for example, substantially the entire drainage tube. The volume analysis systems further comprise a volumetric measurement device placed at some point along the path of the drainage tube. In one embodiment, the volume analysis device is placed at the proximal end of the drainage tube, in close proximity to the patient, which facilitates measurement of other factors such as urine temperature. In alternative embodiments, the volume measurement device may be placed at the distal end of the drainage tube, for example within or adjacent to the housing for the motor that turns the screw element. For example, in FIG. 3, the housing for the motor (303) may also contain, or be conjoined with, a flow meter or other metering device capable of measuring urine volume flow. Such distal placement of the flow meter facilitates integration of the volumetric measurement apparatus with the urine collection vessel, and avoids the encumbrance of bulky elements along the proximal and intermediate sections of the drainage path.

An alternative type of urine sampling is the continuous monitoring of urine for specific biomarkers related to disease state of interest, such as sepsis or acute kidney injury. In such systems, urine samples are withdrawn at regular intervals and subjected to various assays for the detection of analytes, such as biomarkers, chemical compounds, etc. For example, experimental systems are under development to monitor oliguria and other markers of acute kidney injury via continuous monitoring. Likewise, sepsis monitoring is achieved by sampling urine for biomarkers of sepsis. Examples of urine sepsis biomarkers include cadherin 1, haptoglobin, complement 3, alpha-1-antitrypsin, ceruloplasmin, and lysosome associated membrane proteins-1, and biomarkers of acute kidney injury include anacute rise in serum creatinine level. In such systems, the entire urine stream is not required, as only aliquots are sampled. The devices and methods of the invention may be applied in such systems to facilitate the conveyance of fresh urine from the patient to the sample collection vessel or analyzer.

Figure 4:
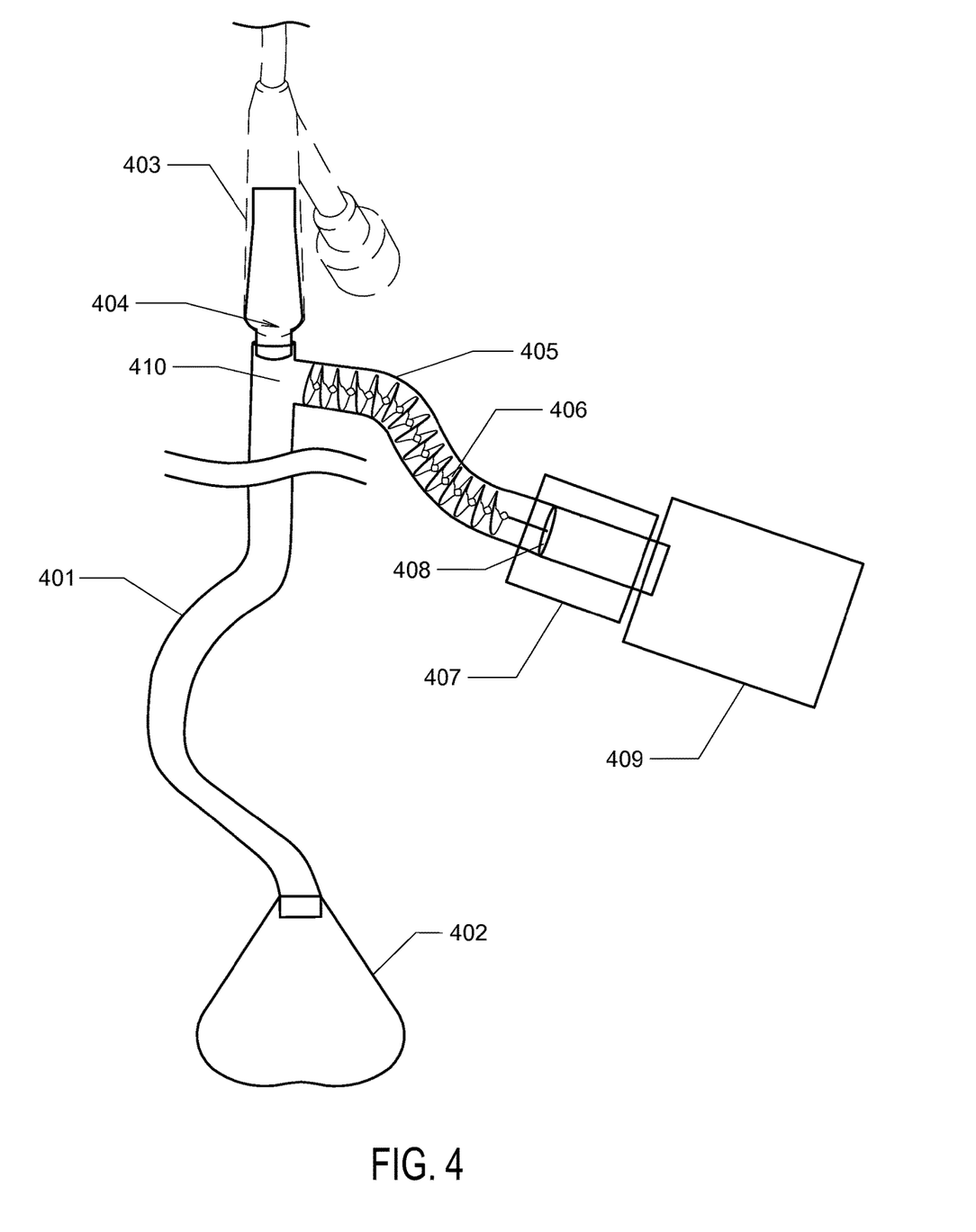
FIG. 4 depicts a schematic diagram of a device comprising an Archimedean screw element, the device used to aid in sampling of fresh urine.

An exemplary urine sampling system is depicted in FIG. 4. In FIG. 4, the drainage outlet of a urinary catheter (403) is connected to the drainage tube by a fitting (404), which may comprise any standard linkage between catheters and drainage tubes, as known in the art. The system depicted in FIG. 4 utilizes a branched junction (410) at or near the proximal end of the drainage tube. On one branch of the tubing (405), the "sampling branch," an Archimedean screw element (406), is driven by a motorized drive element (408) residing in a housing (407). The screw element is used to pull aliquots of fresh urine to a sampling port, or to a sample collection vessel or analysis device (409). The second branch of the drainage tube (401) drains the majority of the urine stream to a urine collection vessel (402).

In branched drainage tubes with a sampling branch, the sampling branch may be located at any point along the drainage tube, for example at the proximal end of the tube, as in FIG. 4, to effect collection of the freshest urine, or at the distal end, to effect a low profile and/or integration with the urine collection vessel.

Figure 5:
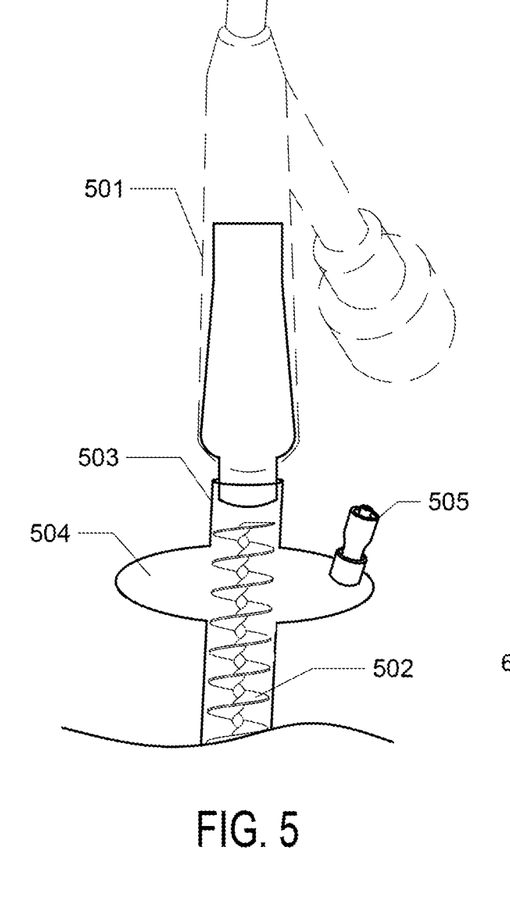
FIG. 5 depicts a schematic diagram of an Archimedean screw drainage system with a flared tube and sample port for facile sampling of urine.
Figure 6:
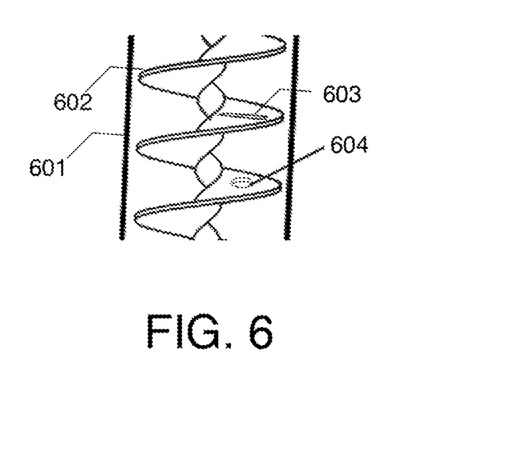
FIG. 6 depicts a section of drainage tubing 601 wherein a flexible screw conveyer 602 is present in the lumen of the tubing. The screw conveyer planar surface has a slit 603 and a hole 604.

In an alternative sampling embodiment, the drainage tube is not branched, but instead comprises an Archimedean screw element and, within the portion of the drainage tube where the Archimedean screw element resides, a sampling port is situated. For example, a valve or Luer-lock fitting may be present in the drainage tube such that samples can be manually withdrawn at regular intervals. In an alternative embodiment, the sampling port is connected to a sampling vessel which can be periodically detached and replaced. In another embodiment, the sampling port is connected to a sampling device which withdraws an aliquot by automated means, such as a continuous or intermittent pumping action. In some implementations, the sampling port is situated at or near the proximal end of the drainage tube to facilitate sampling of the freshest urine, however the sampling port may be located at any position along the drainage path. For example, sampling ports at the end of the drainage path will be sufficient when the drainage system is reliably efficient. In some embodiments, the drainage tube comprises a widened segment wherein urine will pool, increasing the volume of liquid available for sampling. An exemplary drainage tube with sampling port and widened section is illustrated in FIG. 5, wherein the housing contains an Archimedean screw element (502) which is located at or close to the junction between the catheter and the drainage tube (503). This screw element enables the efficient drainage of fresh urine from the catheter (501). A section of the tubing is flared to create a larger volume space (504) from which samples may be periodically or continuously withdrawn from a sample port (505).

Thoracostomy Drainage Systems.

In another aspect, the invention is directed to the use of Archimedean screw elements to aid in the efficient drainage of the chest cavity in a thoracostamy drainage tube system. Thoracostomy drainage tube systems, or "chest tubes," are utilized to provide continuous suction and drainage to the chest cavity, for example in treatment of collapsed lungs. Such systems are prone to blockage by the withdrawal of high viscosity material such as mucus, pus, or blood clots, which block the drainage tube and impede the application of constant suction to the chest cavity. The devices and methods of the invention may be utilized in thoracostamy systems in order to prevent the obstruction of the chest drainage tube by efficiently moving solid and semi-solid materials along the drainage tube. Furthermore, thoracostomy drainage tube systems are also subject to obstruction (decreased drainage and decreased negative pressure) when dependent loops along the tubing fill with fluid/semi-solid material. In such cases, to maintain continuous drainage and negative pressure within the thoracostomy drainage tube, one or more Archimedean screw elements may be utilized at any point from the connection point to the chest tube all the way to the drainage reservoir, for example spanning a section of or substantially all of the length of the tubing. Such elements will aid in the efficient flow of material across dependent loops. Such systems may be used in place of, or in combination with a source of suction.

The devices and methods of the invention may be utilized in any medical context where the clearance of clots, pus, mucus, cellular debris, and other solid or semi-solid materials is desired, and are not limited to thoracostamy systems. For example, Archimedean screw elements may be employed in any medical drainage context, for example in the drainage of wounds and abscesses.

The drainage devices and elements described herein have been described with reference to medical applications. However, it will be understood that the scope of the invention encompasses any application wherein material is moved through flexible tubing, for example in industrial, culinary, and other settings.

Space Medicine.

The devices and methods of the invention advantageously provide a gravity-independent means of moving fluids, semi-solids, slurries, and other materials from a source to a collection vessel. Accordingly, these devices and methods may be employed in low- or zero-gravity environments, i.e. in space. The invention therefore encompasses the use tubing containing one or more Archimedean screw elements in drainage or conveyor systems utilized in space vessels or any other low- or zero-gravity environment. The devices and methods of the invention are directed to any transport of materials within a weightless or semi-weightless environment, including the transport of materials in medical, plumbing, waste disposal, or construction contexts.

In one embodiment, the devices and methods of the invention are directed to medical applications in low or zero gravity environments, including urinary catheter systems, thoracostamy systems, and general surgical or wound care drainage systems.

In one embodiment, the devices of the invention are utilized is used in the transport of human waste. Urination and defecation in space are challenging because human waste does not fall away from the individual as it is expelled from the body. The devices and methods of the invention provide a means of moving human waste away from the individual to a collection or disposal apparatus. For example, an Archimedean element residing within a tubular body can be utilized as a urinal or toilet designed for use in space, wherein the screw can move waste away from the individual and his or her vicinity, for the purpose of collection or disposal.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

The invention claimed is:

1. A medical drainage device, comprising
   a section of flexible tubing, having a proximal end configured to be disposed towards a patient and a distal end disposed towards a collection vessel, wherein the tubing is configured to allow air and fluid to flow through the tubing and wherein the tubing is subject to formation of air-locks from bends or loops in the tubing;
   a source of material, which said material enters the proximal end of the tubing;
   a flexible screw conveyer disposed within the lumen of the tubing and configured to
   promote unobstructed flow of material through the tubing for drainage of the material from the proximal end of the tubing to the distal end of the tubing by mechanically preventing obstructions and airlocks in the tubing; and
   a motor which rotates the screw conveyer;
   wherein
   the flexible screw conveyer comprises a planar screw surface and wherein the planar screw surface comprises slits or holes in the planar screw surface, wherein such slits or holes are configured to allow air ingress in order to maintain the tubing at ambient air pressure.

2. The device of claim 1, wherein
   the source of material is a urinary catheter and the material is urine.

3. The device of claim 1, wherein
   the source of material is a thoracostamy tube and the material is discharge from the thoracic cavity.

4. The device of claim 1, wherein
   the flexible screw conveyer comprises a continuous plane screw.

5. The device of claim 1, wherein
   the flexible screw conveyer comprises a solid screw.

6. The device of claim 1, wherein
   the flexible screw conveyer comprises a polymeric material.

7. The device of claim 6, wherein
   the polymeric material is selected from a group consisting of polypropylene, polyethylene, silicone rubber, polyurethane, epoxy resin, polymethylmethacrylate, polyamides, polyimides, elastomers, fluorocarbons, nylons, polyvinyl, poly olefin and closed cell resin foam.

8. The device of claim 1, wherein
   the flexible screw conveyer comprises a central shaft of one material and a planar screw portion of another material.

9. The device of claim 2, wherein
   the tubing extends substantially from a drainage outflow port of the urinary catheter to the collection vessel.

10. The medical drainage device of claim 1, wherein
    the flexible screw conveyer spans substantially the entire length of the section of flexible tubing.

11. The medical drainage device of claim 1, wherein
    the flexible screw conveyers comprises a central shaft; and
    wherein the motor is present at the distal end of the tubing and is connected to the central shaft of the flexible screw conveyer.

12. A method of
    moving material through a medical drainage system
    wherein the medical drainage system comprises flexible tubing;
    wherein the tubing is configured to allow air and fluid to flow through the tubing and wherein the tubing is subject to formation of air-locks from bends or loops in the tubing;
    the method comprising the actions of
    connecting the proximal end of the tubing to a source of material and the distal end of the tubing to a collection vessel, wherein the material enters into the tubing;
    wherein an Archimedean screw element comprising a flexible screw conveyer is disposed within the tubing;
    wherein the flexible screw conveyer comprises a planar screw surface and wherein the planar screw surface comprises openings in the planar screw surface comprising slits or holes, wherein such slits or holes are configured to allow air ingress in order to maintain the tubing at ambient air pressure:
and
rotating the flexible screw conveyer such that the screw conveyer mechanically prevents obstructions and airlocks in the tubing,
wherein the Archimedean screw is rotated by the use of a motor in connection with the flexible screw conveyer.

13. The method of claim 12, wherein the medical drainage system is a urine collection system.

14. The method of claim 12, wherein the medical drainage system is a thoracostamy system.

15. The method of claim 12, wherein the method is performed in a low or zero gravity environment.

16. The method of claim 15, wherein the material is selected from the group consisting of urine, excrement, and discharge from a patient's thoracic cavity.

* * * * *